United States Patent [19]

Igaue et al.

[11] Patent Number: 5,034,007
[45] Date of Patent: Jul. 23, 1991

[54] MANUFACTURING METHOD FOR DISPOSABLE CLOTHING ITEMS

[75] Inventors: Takamitsu Igaue, Kawanoe; Yasushi Inoue, Doimachi, both of Japan

[73] Assignee: Uni-Charm Corporation, Ehime, Japan

[21] Appl. No.: 483,807

[22] Filed: Feb. 23, 1990

[51] Int. Cl.[5] .................. A61F 13/00; B32B 31/00
[52] U.S. Cl. .............................. 604/365; 604/380; 604/385.1; 428/78; 428/230; 428/231; 156/160; 156/229; 156/269
[58] Field of Search .................. 156/160, 229, 269; 428/78, 198, 280, 231; 604/365, 380, 385.1

[56] References Cited

U.S. PATENT DOCUMENTS

| | | | |
|---|---|---|---|
| 1,545,557 | 7/1925 | Guignard | 604/377 |
| 3,666,611 | 5/1972 | Joa | 604/365 |
| 4,413,623 | 11/1983 | Pieniak | 604/365 |
| 4,886,697 | 12/1989 | Perdelwitz, Jr. et al. | 604/385.1 |

Primary Examiner—Stephen C. Pellegrino
Assistant Examiner—Gary Jackson
Attorney, Agent, or Firm—Fred Philpitt

[57] ABSTRACT

A method for making disposable absorbent articles which includes cutting a sheet into two elongated webs so that one edge of each web is straight and the other edge has alternating concave and convex portions, affixing the webs to a water-impervious backing sheet so that the straight edge portions thereof face each other and the alternating concave-convex portions face outwardly.

6 Claims, 4 Drawing Sheets

MANUFACTURING METHOD FOR DISPOSABLE CLOTHING ITEMS

This invention is related to a manufacturing method for disposable diapers and disposable diaper types of disposable clothing items. More specifically, it is related to a manufacturing method for said clothing items having a flap formed in concave sections which surrounds the thighs of the wearer.

BACKGROUND

Up to now, as one clothing item, for example, a pants type of disposable diaper in which concave sections have formed flaps on both sides which surround the thighs of the wearer have been offered for practical use. The fitting properties for the body of the wearer are vastly improved by the diaper having concave sections on both side flaps. The concave sections made in this way are formed by cutting away both side sections of a web which is permeable to liquids and a web is impermeable to liquids which form the obverse and the reverse. Because there is no way to reuse this cut away flap, it is thrown away. Generally a nonwoven cloth or such is used for the web which is permeable to liquids which forms the obverse of the diaper, and plastic film or such is used for the web which is impermeable to liquids which forms the reverse of the diaper, but the former has a high production cost compared to the latter. It is desirable to use the obverse web which is high in production cost for efficiency, but as was mentioned before, in order to form the concave sections around the thighs, the practice of cutting away both side sections of the obverse web is very expensive, and this is an important factor in producing the high cost of the entire diaper.

Therefore, this invention devises a reduction of the production cost of disposable diapers and such clothing items, and in order to design effective use and economy for the obverse web, the formation of the concave section around the thighs without cutting away both side sections of the obverse web is taken as the problem.

THE INVENTION GENERALLY

This invention utilizes the following two manufacturing methods for the purpose of eliminating the above-mentioned problem.

The obverse web is cut so as to create a line which is periodically concave and convex in the lengthwise direction in between both side edges of a single sheet of an obverse web of a comparatively wide width, and two sheets of a continuous divided obverse web are formed. These are symmetrically arranged so that, along with the concave sections which were formed by the cut facing the outer sides, these concave sections are aligned with each other. Both outer sections of these two sheets of continuous divided obverse webs are placed on a continuous reverse web, and both inner edges of these two sheets of continuous divided obverse webs are placed on both side sections of the separate obverse web which has been arranged in the area of the vicinity of the reverse web and these are bonded. In this case, it is necessary to form a concave section in the reverse web also, which is arranged so as to make the concave sections of the divided obverse webs coincide, but for this formation, generally, methods such as cutting away the reverse web sections along the rim of said concave edge sections after the divided obverse web in which the concave sections have been formed in both edge sections is layered and bonded to the reverse web, and a method in which the divided obverse web which has formed the concave section in both edge sections is layered onto a reverse web in which concave sections have been formed by cutting away both side sections so that these concave sections coincide can be offered.

For another manufacturing method, as the continuous obverse web, a sheet wider than the obverse web in the above-mentioned method is used, and both outer edge sections which correspond to both inner edges of the divided obverse web in the above-mentioned manufacturing method are aligned and layered directly on one another and bonded. The rest is exactly the same as the above-mentioned manufacturing method.

In the above-mentioned manufacturing method, the obverse web which is continuously bonded is cut in the width direction so that the above-mentioned concave section is nearly in the center section in the lengthwise direction in the individual clothing items, and individual clothing items are obtained. Depending on requirements, the individual clothing items are made so as to have other construction materials such as abosrbent materials and elastic materials around the legs, and, needless to say, these front and reverse webs can be arranged in a continuous process.

RESULTS OF THE INVENTION

According to this invention, two sheets of divided obverse webs having concave edge sections around the legs are formed from one sheet of obverse web having a comparatively high production cost and arranged and bonded on a reverse web. Because said concave sections are made to coincide with concave edge sections around the legs which have been formed in the reverse web and form flaps on both sides, one section of the obverse web is not cut away and discarded; this can be effectively utilized and economized, and for this reason, the production costs of the clothing items can be reduced and said items can be offered to the consumer at a low cost.

DESCRIPTION OF PREFERRED EMBODIMENTS

The method of this invention is explained below, using disposable diapers as an example and referencing the figures. However, the equipment for the purpose of manufacturing disposable diapers is publicly known to persons in this industry, and since the method of this invention also basically manufactures by using publicly known equipment, said equipment is not shown in the figures.

Figure 1:
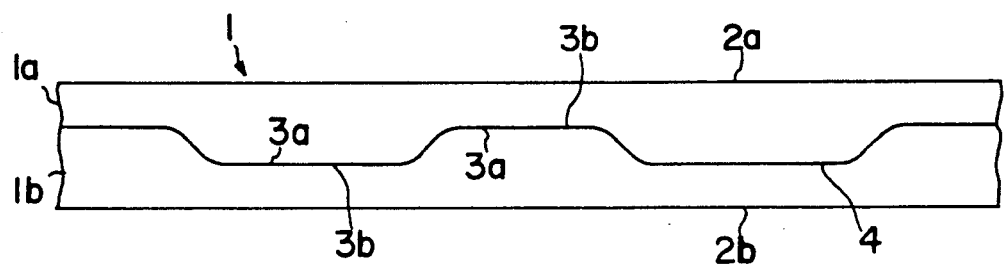
FIG. 1 is partial plane view of the process for forming the divided obverse web for the application examples of the method of this invention.

In FIG. 1, divided obverse webs (1a, 1b) are formed having concave section (3a) and convex section (3b) positioned periodically in the lengthwise direction means by cutting obverse web (1) so as to create concave and convex line (4) periodically in the lengthwise direction in the center section between both edge sections of continuous obverse web (1) of the desired width having substantially parallel edges (2a, 2b).

Figure 2:
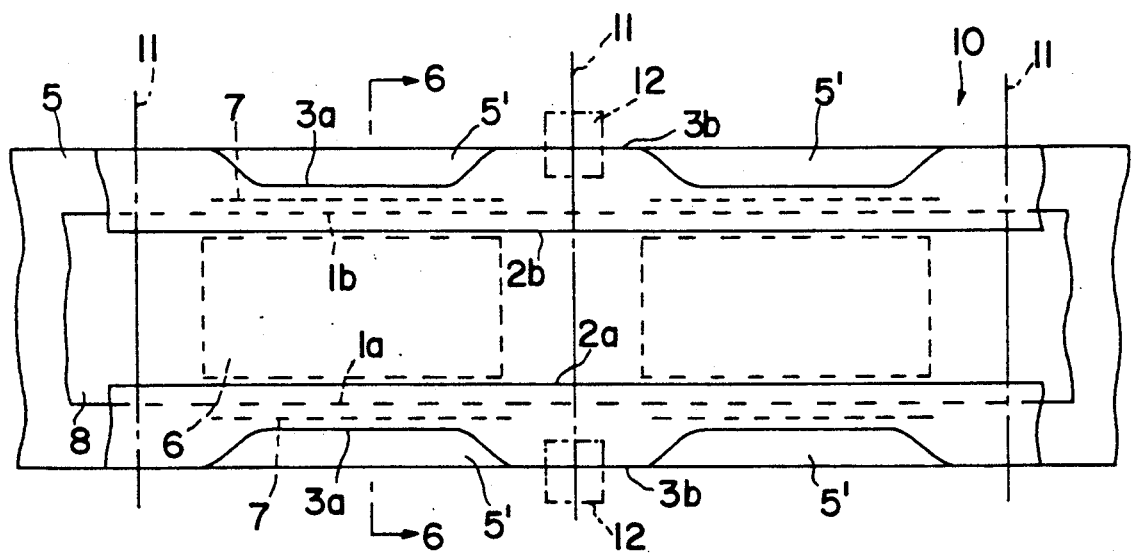
FIG. 2, FIG. 3, FIG. 4, and FIG. 5 are partial plane views of the process in which disposable diapers are manufactured by using a divided obverse web.
Figure 6:
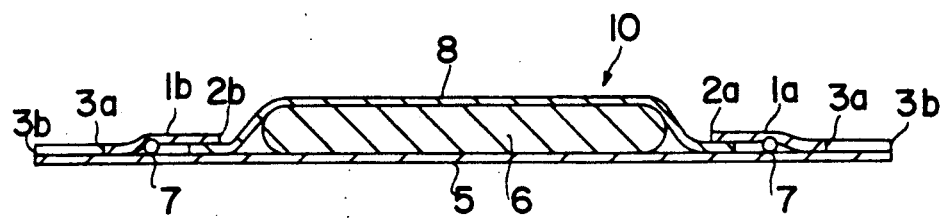

As is shown in FIG. 2 (see also FIG. 6), the absorbent material (6) at the desired spacing in the lengthwise direction of continuous reverse web (5), and elastic material (7) which expands and contracts in the lengthwise direction of the reverse web section on both sides of said absorbent section are individually installed through the medium of adhesive methods. Further, continuous separate obverse web (8) which is narrower in width than said reverse web is layered with absorbent material (6) and elastic material (7) interposed, except for both side sections of reverse web (5).

Divided obverse webs (1a, 1b) are separated and are symmetrically arranged in the width direction facing each other with edges (2a, 2b) on the inside and concave section (3a) on the outside, and concave sections (3a, 3a) are aligned with each other. In making of concave sections (3a, 3a) face outward in this manner. In FIG. 1, either divided obverse webs (1a, 1b) are crossed over and the upper side divided web (1a) is moved to the lower side, and the lower side divided obverse web (1b) is moved to the upper side and exchanged, or divided obverse webs (1a, 1b) are individually reversed 180°. In FIG. 2, divided obverse webs (1a, 1b) are arranged by being crossed over.

Divided obverse webs (1a, 1b) arranged in this manner are layered both side sections of reverse web (5) where obverse web (8) is not layered and on both outside sections of both side sections of obverse web (8), and the outer edges of convex sections (3b) of divided obverse webs (1a, 1b) are made to substantially align with the outside edge of reverse web (5), and at least the layered sections are bonded by an adhesive method. Section (5') of reverse web (5) which is enclosed by concave section (3a) of divided obverse webs (1a, 1b) is cut away so as to align with said concave section.

Figure 3:
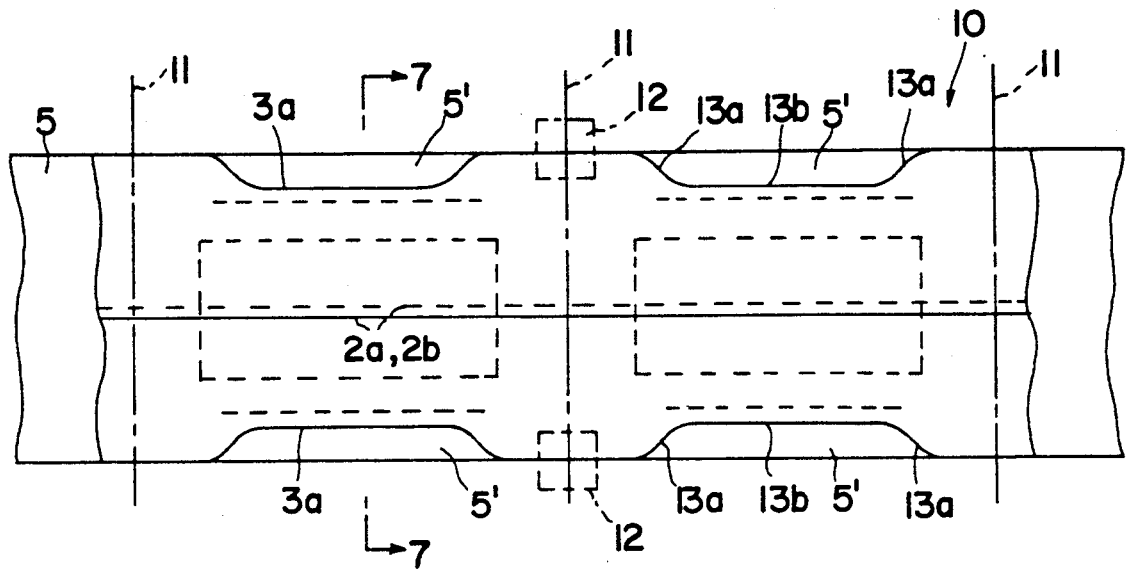
Figure 7:
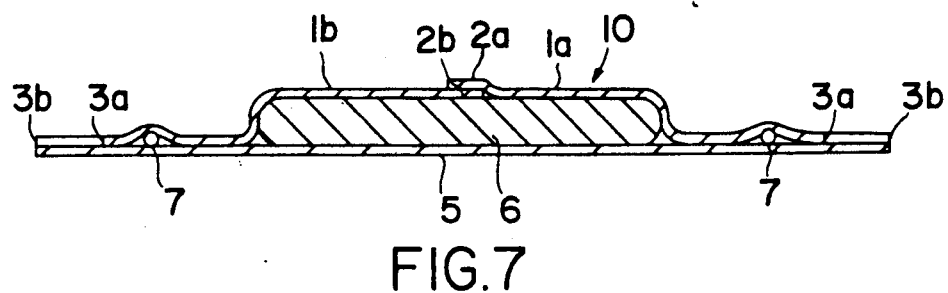
FIG. 6, FIG. 7, FIG. 8, and FIG. 9 are cross sections of FIG. 2 line 6—6, FIG. 3 line 7—7, FIG. 4 line 8—8, and FIG. 5, line 9—9.

Another application example is shown in FIG. 3 (see also FIG. 7). In the application example which is shown in FIG. 3 also, the obverse web which is shown in FIG. 1 is used. When divided obverse webs (1a, 1b) having concave and convex sections (3a, 3b) are formed, the respective arrangement of absorbent material (6) on reverse web (5) and elastic material (7) in the reverse web section which is on both sides of said absorbent material is the same as in the case of the application example shown in FIG. 2, but an obverse web (1) which is broader in width than in the case of the application example in FIG. 2 is used. Also, in the case of the application example shown in FIG. 3, edges (2a, 2b) of divided obverse webs (1a, 1b) are layered on the other without using obverse web (8) and bonded by an adhesive method. Processes other than this are all the same as in the case of the application example shown in FIG. 2.

Figure 4:
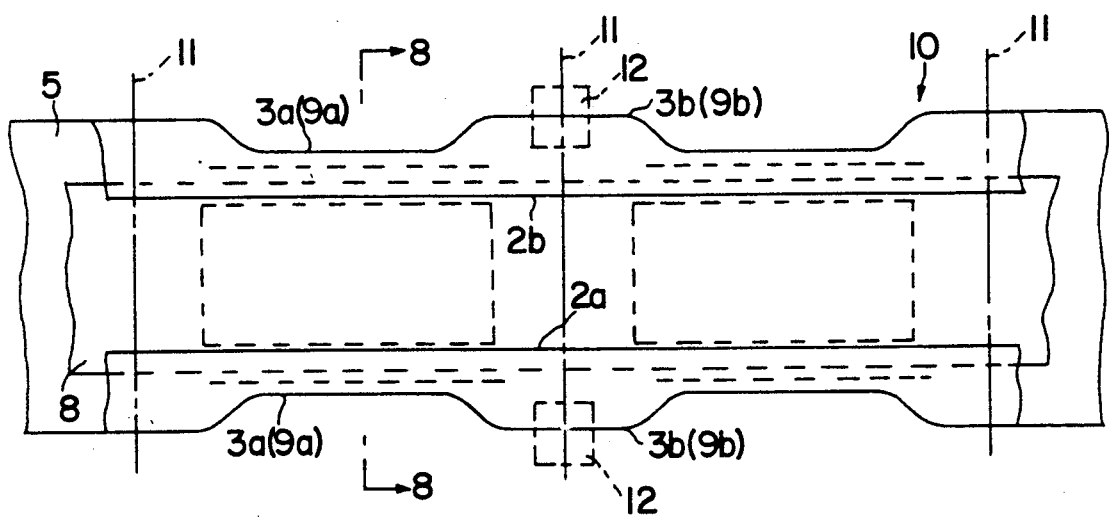
Figure 5:
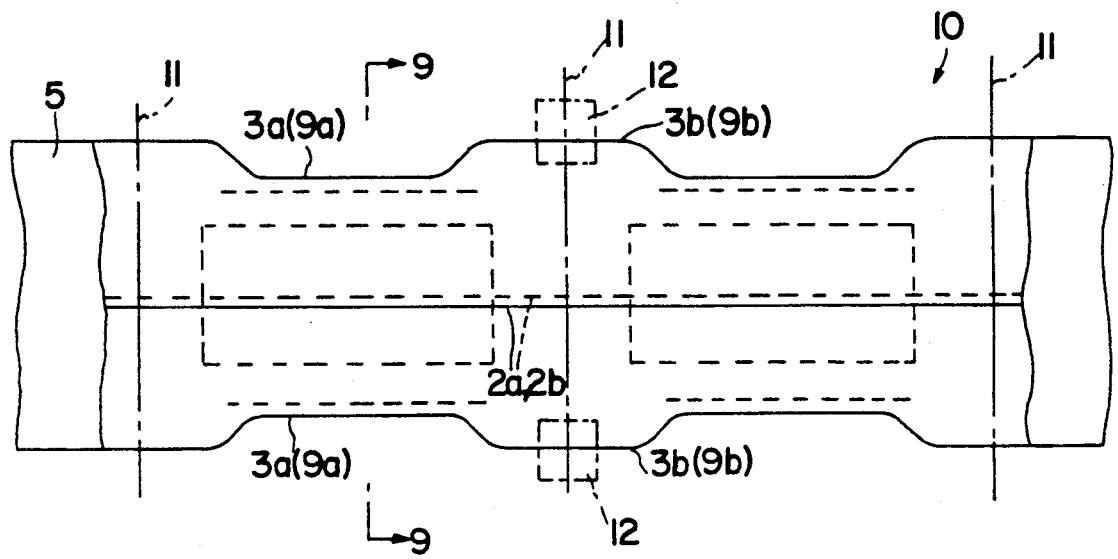
Figure 9:
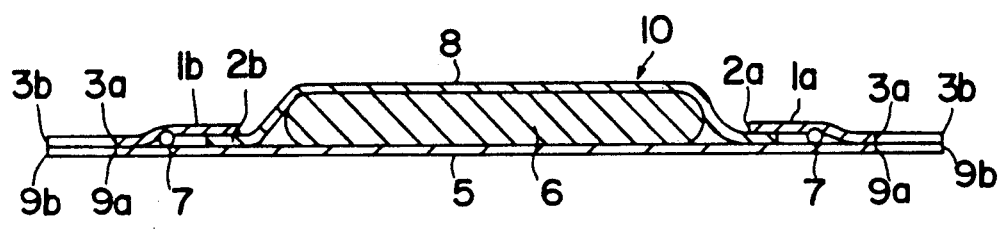
Figure 8:
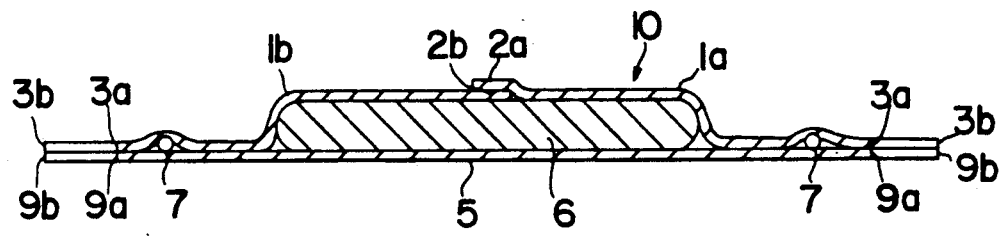

Other application examples are shown in FIG. 4 (see also FIG. 8) and FIG. 5 (see also FIG. 9), respectively. In the application examples shown in FIG. 4 and FIG. 5, the concave and convex sections (3a, 3b) of divided obverse webs (1a, 1b) and the respective matching concave and convex edges (9a, 9b) are formed, and except for the matching of these concave sections (3a, 9b) and these convex sections (3b, 9b), they are the same as the application examples shown in FIG. 2 and FIG. 3, respectively. In the event that concave sections (3a, 9a) are slightly misaligned, they can be made to match by cutting away their outer edges at the same time.

After constructing continuous diaper (10) as is shown in the application examples which are shown in FIG. 2 through FIG. 5, individual diapers can be obtained by imaginary cutting line (11) in convex section (3b) which is located in the lengthwise direction of these divided obverse webs (1a, 1b); in other words, in the width direction between opposite facing absorbent materials (6).

In each application example, tape fastener (12) (shown by the dot and bar line) of twice the width of the desired tape fastener is attached on cutting line (11), and when individual diapers are obtained by cutting on said cutting line (11), simultaneous with this cutting, said tape fasteners are also made so as to divide in two. However, tape fasteners of the desired width for the individual diapers (12) can also be formed beforehand and affixed at the desired locations. The base sections of tape fasteners (12) are generally affixed to reverse web (5), but they can also be affixed interposed between each divided obverse web (1a, 1b) 8 and/or reverse web (5).

In each of the application examples above, depending on the product, the possession of absorbent material (6), elastic material (7), and tape fastener (12) are not absolutely necessary, but in the event these are necessary, absorbent material (6) is generally bonded to obverse webs (1a, 1b) and/or reverse web (5) by an adhesive method, and elastic material (7) is generally bonded to obverse webs (1a, 1b) and/or reverse web (5) by an adhesive method. Also, elastic material (7) can be attached so as to curve, following the curved edges of concave sections (3a, 9a). Hot melt type adhesives and fusing (including fusing by means of ultrasonic waves) can be used for these adhesive methods and the adhesive methods already presented.

It is not shown in the figures, but, depending on circumstances, reverse web (5) can also be formed like divided obverse webs (1a, 1b), and the desired sections bonded by an adhesive method. In the event reverse web (5) is formed like divided obverse webs (1a, 1b), obverse web (1) and reverse web (5) can be layered on the other and cut simultaneously. The application of this type of method is probably easy for people in this industry when they consider the above presentation related to divided obverse webs (1a, 1b). Also, it is not shown in the figures, but the fact that the elastic material in the thighs of the individual diapers can also be attached between the webs during the connecting process of the obverse webs is probably clear to persons in this industry. One more thing, it is not shown in the figure, but if I speak using the right half of FIG. 3 as representative, depending on circumstances, the lengthwise edges of line sections (13a) can be cut into, and reverse web section (5') can be folded back and fastened to the upper surface of divided obverse webs (1a, 1b) through section (13b) between these, without cutting away reverse web section (5').

As for the materials for obverse web (1, 8), reverse web (5), absorbent body (6), elastic material (7), and tape fastener (12), materials which have been used in disposable diapers up to now can be utilized. For example, for obverse web (1, 8), nonwoven cloth and porous plastic film; for reverse web (5), plastic film which either allows air to flow through or does not allow air to flow through, or a lamination of this and nonwoven cloth; for absorbent material (6), a mixture of cotton pulp and high absorbency polymer powder; for elastic material (7), natural or synthetic rubber, polyurethane rubber, or materials which exhibit expansion and contraction properties by heat processing; and for tape fastener (12), pressure sensitive adhesive tape; can be used. Preferably, in the application examples shown in FIG. 2 and FIG. 4, a material of nonwoven cloth which is water resistant and to which air passage properties and properties of being impermeable to liquids have been added can be used for the material for divided obverse webs (1a, 1b).

We claim:

1. A method for manufacturing disposable absorbent items which comprises the steps of
    (a) forming two elongated webs of material (1a, 1b) by cutting the interior an elongated sheet of material (1) lengthwise along a cutting line (4) so that each of the resulting two elongated webs (1a, 1b) has two elongated sides, one side (2a, 2b) being substantially straight and one side having alternating concave sections (3a) and convex sections (3b),
    (b) affixing the two elongated webs of material (1a, 1b) to the side portions of an elongated water impervious sheets (5) along two spaced apart lines so that
        (1) the elongated straight sides (2a, 2b) of the webs (1a, 1b) extend inwardly from the side edges of said elongated sheet (5),
        (2) the alternating concave (3a) and convex (3b) sections of the webs (1a, 1b) extend outwardly toward the side edges of said elongated sheet (5), and
        (3) the concave sections (3a) of the two webs are laterally aligned with each other and the convex sections (3b) of the two webs are laterally aligned with each other,
    (c) depositing an absorbent material (6) on said elongated sheet (5) in the area between said two affixed elongated webs of material (1a, 1b), and
    (d) severing the foregoing assemblage at spaced apart intervals along the length of the assemblage with severing lines that are transverse to the length of said assemblage and which pass laterally through the middle of each convex section (3b).

2. The method of claim 1 wherein when said two elongated webs of material (1a, 1b) are affixed, said elongated straight sides (2a, 2b) overlap each other.

3. The method of claim 2 wherein the sides of said elongated water-impervious sheet (5) are contoured at spaced apart intervals and these contoured sections (9a) aligned with the concave sections (3a) of the two elongated webs of material (1a, 1b) that are affixed to the water-impervious sheet (5).

4. The method of claim 1 wherein includes placing a further elongated web of material (8) over said absorbent material (6), the width of this further elongated web of material (8) being less than the width of said elongated sheet (5), and positioning said elongated straight sides (2a, 2b) over the side edges of said further elongated web (8).

5. The method of claim 4 wherein the sides of said elongated water-impervious sheet (5) are contoured at spaced apart intervals and these contoured sections (9a) aligned with the concave sections (3a) of the two elongated webs of material (1a, 1b) that are affixed to the water-impervious sheet (5).

6. The method of claim 1 wherein the sides of said elongated water-impervious sheet (5) are contoured at spaced apart intervals and these contoured sections (9a) aligned with the concave sections (3a) of the two elongated webs of material (1a, 1b) that are affixed to the water-impervious sheet (5).

* * * * *